United States Patent [19]

Jain

[11] Patent Number: 5,080,664
[45] Date of Patent: Jan. 14, 1992

[54] DEVICE FOR HOLDING A VEIN DURING VASCULAR SURGERY

[76] Inventor: Krishna M. Jain, 8405 Plover, Kalamazoo, Mich. 49002

[21] Appl. No.: 584,457

[22] Filed: Sep. 18, 1990

[51] Int. Cl.⁵ .............................................. A61B 17/00
[52] U.S. Cl. .................................... 606/148; 606/190
[58] Field of Search ............... 606/125, 148, 150–232

[56] References Cited

U.S. PATENT DOCUMENTS

| | | | |
|---|---|---|---|
| 3,410,269 | 11/1968 | Hovick | 606/125 |
| 3,533,411 | 10/1970 | McKnight | 606/125 |
| 4,372,302 | 2/1983 | Akerlund | 606/148 |
| 4,545,373 | 10/1985 | Christoudia | 606/148 |
| 4,553,543 | 11/1985 | Amarasinghe | 606/148 |
| 4,651,733 | 3/1987 | Mobin-Uddin | 606/150 |
| 4,784,139 | 11/1988 | Demos | 606/148 |
| 4,911,164 | 3/1990 | Roth | 606/148 |
| 4,946,462 | 8/1990 | Watanabe | 606/148 |
| 4,959,067 | 9/1990 | Muller | 606/190 |

Primary Examiner—Stephen C. Pellegrino
Assistant Examiner—Gary Jackson
Attorney, Agent, or Firm—Varnum, Riddering, Schmidt & Howlett

[57] ABSTRACT

A holding device for use during surgical procedures involving tubular body ducts includes a shank portion and a terminal portion. The terminal portion has a bulbous section at the terminus of the rod. The outer surface of the terminal portion is free of discontinuities, and the bulbous section has a cross-sectional dimension slightly less than the diameter of the tubular body duct. The terminal portion can be received within the body duct so that the bulbous section will resist withdrawal when the body duct is tied to the terminal portion.

20 Claims, 1 Drawing Sheet

DEVICE FOR HOLDING A VEIN DURING VASCULAR SURGERY

BACKGROUND OF THE INVENTION

1. Field of the Invention

The invention relates generally to medical devices utilized during surgical suturing, specifically, the art of anastomosis. In particular, the invention relates to a device for holding tubularly-shaped body ducts, such as blood vessels, during anastomosis.

2. Scope of the Prior Art

When performing heart surgery, and other surgery involving blood vessels and other body ducts, the job of anastomosing one vessel to another is normally performed by stitching edges of blood vessel openings together. The need for satisfactorily holding adjacent blood vessels during anastomosis is well recognized, and various solutions have been developed for meeting the need.

During vein bypass graft surgery, for example, forceps are commonly used to hold and suspend the slanted or beveled open end (fish mouth opening) of a vein in close proximity to the opening on the wall of the aorta while sutures are being taken. However, the forceps can easily slip from its position during the anastomosis. Moreover, the inner wall of the vein is very susceptible to damage due to the holding or stretching of the vein by the forceps. Yet further, the vein has a tendency to collapse which only increases the difficulty in suturing the graft to the aorta.

Another solution is disclosed in U.S. Pat. No. 4,651,733 issued to Mobin-Uddin. The Mobin-Uddin device is an elongated rod having a holder on one end, a shank portion in the middle, and a prong on the other end. The prong has a sharply pointed hook extending laterally, and preferably in a rearwardly direction, therefrom. The prong is inserted into the open end of a blood vessel until the hook reaches the distal end of the vessel. The hook pierces the vessel wall to lock the vessel onto the prong whereupon the device "holds" the blood vessel in the desired position at the outset of the anastomosis.

The invention provides a means for holding a vein during vascular surgery without piercing the wall of the vein, and without placing unnecessary stresses on the vein. In one aspect of the invention, a holding device is provided for holding a vein during vascular surgery. The device comprises a substantially rigid elongated rod having a shank portion and a terminal portion connected to the shank portion. The terminal portion has a bulbous section spaced from the shank portion, and the outer surface of the terminal portion is free of discontinuities. The bulbous section has a cross-sectional dimension slightly less than the diameter of the vein so that the terminal portion can be received within the vein. When the diameter of the vein between the bulbous section and the shank portion is reduced, the bulbous section will resist withdrawal of the vein.

Preferably, the terminal portion has a terminus and the bulbous section is located at the terminus. Also, preferably the terminal portion will not be co-linear with the shank portion.

In another aspect of the invention, the rod is formed in one piece, and the shank portion has means for gripping the rod. Preferably, the shank portion is longer than the terminal portion.

The shank portion and terminal portion can be integrally formed so that the elongated rod is a unitary structure.

In another aspect of the invention, a holding assembly is provided for holding a vein during vascular surgery. The assembly comprises a substantially rigid elongated rod having a shank portion and an integral terminal portion. Engagement means are provided to cause the terminal portion to functionally engage and retain the interior wall of the vein against movement relative to the rod without placing point stresses on the interior wall. Preferably, the engagement means comprises a bulb integrally connected to the terminal portion. The engagement means further comprises a tie adapted to be disposed around the outer wall of the vein.

In yet another aspect of the invention, a method is described for holding a vein during vascular surgery. The method comprises the steps of providing a substantially rigid elongate rod having a shank portion and a terminal portion. The terminal portion has a bulbous section spaced from the shank portion, and the outer surface of the terminal portion is free of discontinuities. The bulbous section is inserted into the vein so that a portion of the vein is disposed between the bulbous section and the shank portion. The portion of the vein between the bulbous section and the shank portion is then reduced, and the shank portion of the rod can be grasped to hold the vein in a predetermined position for surgery. Preferably, the diameter of the vein is reduced by tying a cord around the portion of the vein between the bulbous section and the shank portion.

BRIEF DESCRIPTION OF THE DRAWINGS

The invention will now be described with reference to the following drawings in which.

DETAILED DESCRIPTION OF THE INVENTION

Figure 1:
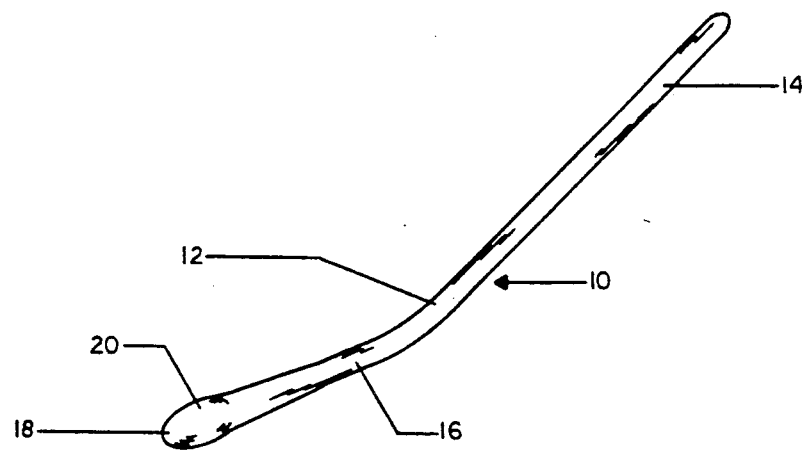
FIG. 1 is an isometric view of a blood vessel holding device of the invention.

Referring to FIG. 1, a holding device 10 for use in surgical procedures involving tubular body ducts is illustrated. The device 10 is particularly adapted for use in holding flexible, expandable tubular body ducts such as blood vessels during anastomosis. The device 10, according to the invention, comprises an elongated body or rod 12 having a substantially straight, cylindrical shank portion 14 and a terminal portion 16 extending from the shank portion.

The terminal portion 16 may extend colinearly with the shank portion 14 or, as illustrated in FIG. 1, extend at an angle. Preferably, the terminal portion 16 will extend at an angle of approximately 20 degrees relative to the axis of the shank portion 14. The device 10 typically has an overall length of less than eight inches, with the shank portion 14 being longer than the terminal portion 16, thereby providing for convenient manipulation of the device. Preferably, the device will be formed of a lightweight, substantially rigid material such as plastic, although other materials such as noncorrosive metals are acceptable.

At the terminus 18 of the terminal portion 16 is a bulbous section 20. The bulbous section 20 has a cross section noticeably larger than the cross section of the terminal portion 16 and the shank 14. Further, the bulbous section 20 has a smooth, rounded exterior surface. The outer surface of the bulbous section 20 and the terminal portion 16 is free of discontinuities.

Figure 2:
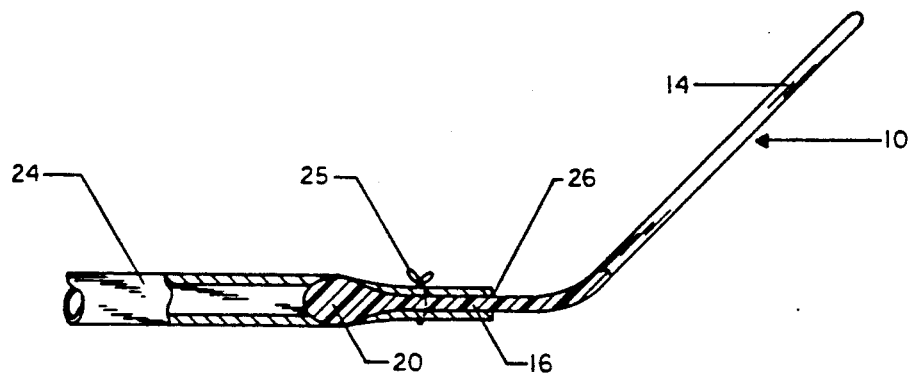
FIG. 2 is a partial cross-sectional view of the holding device in use with a blood vessel.

FIG. 2 shows a partial cross-sectional, longitudinal view of the device 10 in use. It will be seen that the bulbous section 20 of the terminus 18 is inserted into the end 22 of a blood vessel 24. Most tubular body ducts, and blood vessels in particular, are flexible and subject to collapse. The smooth surface of the holding device 10, and particularly the bulbous section 20 on the terminal portion 16, permits the device 10 to be inserted into the open end 22 of the blood vessel 24. Preferably, the cross-sectional dimension of the bulbous section 20 is only slightly less than the diameter of the unexpanded blood vessel 24, and the bulbous section itself has no surface discontinuities. The bulbous section 20 is easily received by the walls of the blood vessel 24, thus maintaining the vessel open. Preferably, about one inch of the terminal portion 16 is inserted into the vessel 24. A tie 25 is placed around the blood vessel 24 and the terminal portion 16 to reduce the diameter of the blood vessel 24 to less than the cross-sectional dimension of the bulbous section 20. The vessel walls simultaneously grip the bulbous portion. Thus, the blood vessel 24 is secured onto the holding device 10. With the holding device thus secured, the shank portion 14 may be grasped and the end 22 of the blood vessel 24 may be manipulated into a position adjacent an adjoining body tissue to be sutured thereto. To facilitate grasping the shank 14, the outer surface thereof may be rough and knurled or coated with a high-friction material.

Figure 3:
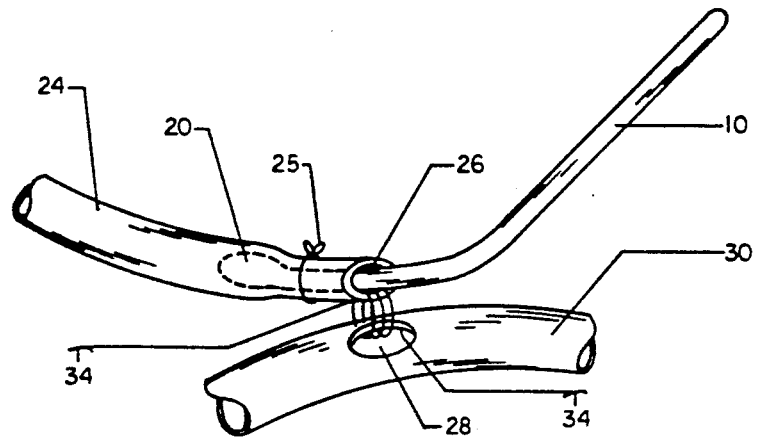
FIG. 3 illustrates a suturing method employing the device of this invention.

FIG. 3 illustrates an end-to-side technique of anastomosis employing a holding device according to the invention. The device 10 is shown inserted into an opening 26 in the end of a vein 24. The opening 26 is disposed adjacent and in proximate facing relationship with respect to a complementary opening 28 in the wall of an adjacent blood vessel 30. As is conventional in anastomosis, the openings 26, 28 are oval, and the direction of the oval 28 relative to the axis of a blood vessel depends upon the direction of approach of the vessel 24 with respect to the vessel 30. The bulbous portion 20 in the opening 26 prevents collapse of the opening during the anastomosis procedure. The holder 10 retains the opening 26 in proximate position with respect to the opening 28 until sutures 32, taken by means of attached needles 34, can support the opening 26 in the proximate position. When enough stitches have been taken, for example along slightly more than one-half of the circumference of the opening, the tie 25 is released, and the holder 10 may be removed from the openings 26, 28, whereupon the existing sutures may be tightened, and the suturing completed by taking additional stitches until the vessel 24 is secured to the vessel 30.

Reasonable variation and modifications are possible within the scope of the foregoing disclosure and drawings without departing from the spirit of the invention which is defined by the appended claims.

The embodiments of the invention in which an exclusive property or privilege is claimed are defined as follows:

1. A holding device for holding a vein during vascular surgery, said device comprising a substantially rigid elongated rod having a shank portion, and a terminal portion connected to the shank portion, said terminal portion having a bulbous section spaced from the shank portion, the outer surface of the terminal portion being free of discontinuities, and the bulbous section having a cross-sectional dimension slightly less than the diameter of the vein so that the terminal portion can be received within the vein and the bulbous section resist withdrawal therefrom when the diameter of the vein between the bulbous section and the shank portion is reduced.

2. A holding device according to claim 1 wherein the terminal portion has a terminus and the bulbous section is located at the terminus.

3. A holding device according to claim 2 wherein the terminal portion is not colinear with the shank portion.

4. A holding device according to claim 3 wherein the rod is formed in one piece.

5. A holding device according to claim 4 wherein the shank portion has means for gripping the rod.

6. A holding device according to claim 5 wherein the shank portion is longer than the terminal portion.

7. A holding device according to claim 1 wherein the terminal portion is not colinear with the shank portion.

8. A holding device according to claim 7 wherein the rod is formed in one piece.

9. A holding device according to claim 1 wherein the rod is formed in one piece.

10. A holding device according to claim 1 wherein the shank portion has means for gripping the rod.

11. A holding device according to claim 1 wherein the shank portion is longer than the terminal portion.

12. A holding assembly for holding a vein during vascular surgery comprising a substantially rigid elongated rod having a shank portion and an integral terminal portion; engagement means for causing the terminal portion to functionally engage and retain the interior wall of the vein against movement thereof relative to the rod without placing point stresses on the interior wall.

13. A holding device according to claim 12 wherein the engagement means comprises a bulb integrally connected to the terminal portion.

14. A holding device according to claim 13 wherein the outer surface of the bulb in combination with the terminal portion is free of discontinuities.

15. A holding device according to claim 13 wherein the engagement means further comprises a tie adapted to be disposed around the outer wall of the vein.

16. A holding device according to claim 12 wherein the shank portion and the terminal portion are integral.

17. A holding assembly for holding a vein during vascular surgery comprising:
a substantially rigid elongate rod having a shank portion and a terminal portion, said terminal portion having a bulbous section spaced from the shank portion, the outer surface of the terminal portion being free of discontinuities, and the bulbous section having a transverse cross-sectional dimension slightly less than the diameter of the vein; and
means for reducing the diameter of the vein whereby the bulbous section can be received within the vein and resist withdrawal therefrom when the diameter of the vein between the bulbous section and the shank portion is reduced by the reducing means and the vein can thereby be held by grasping the shank portion.

18. A holding assembly according to claim 17 wherein the reducing means comprises a tie adapted to be disposed around the outer wall of the vein.

19. A method of holding a vein during vascular surgery comprising:

providing a substantially rigid elongate rod having a shank portion and a terminal portion, said terminal portion having a bulbous section spaced from the shank portion, the outer surface of the terminal portion being free of discontinuities, and the bulbous section having a transverse cross-sectional dimension slightly less than the diameter of the vein;

inserting the bulbous section into the vein so that a portion of the vein is disposed between the bulbous section and the shank portion;

reducing the diameter of the portion of the vein between the bulbous section and the shank portion; and grasping the shank portion to hold the vein in a predetermined position for surgery.

20. A method of holding a vein according to claim 19 wherein the diameter is reduced by tying a cord around the portion of the vein between the bulbous section and the shank portion.

* * * * *